United States Patent [19]

Stoeckl

[11] Patent Number: 5,300,926
[45] Date of Patent: Apr. 5, 1994

[54] MEDICAL APPARATUS, HAVING A SINGLE ACTUATING DEVICE

[75] Inventor: Klaus Stoeckl, Bensheim, Fed. Rep. of Germany

[73] Assignee: Siemens Aktiengesellschaft, Munich, Fed. Rep. of Germany

[21] Appl. No.: 694,634

[22] Filed: May 2, 1991

[30] Foreign Application Priority Data

May 9, 1990 [EP] European Pat. Off. ........ 90108740.3

[51] Int. Cl.⁵ .................... G06K 15/18; A61M 31/00; A61B 10/00
[52] U.S. Cl. ................. 345/157; 364/413.01; 128/713; 345/145
[58] Field of Search .................. 200/86.5; 364/413.01, 364/413.28; 433/28, 98, 101; 74/478, 512, 560; 341/20, 21; 273/148 B, 85 G; 128/661.1, 713; 178/18; 340/706, 709, 710, 712; 395/56, 57, 161; 606/169; 604/22; 434/45; 318/280-286, 490, 466-469

[56] References Cited

U.S. PATENT DOCUMENTS

| | | | |
|---|---|---|---|
| 3,980,848 | 9/1976 | Schulz et al. | 200/86.5 |
| 4,180,812 | 12/1979 | Kaltenbach et al. | 340/706 |
| 4,383,167 | 5/1983 | Gmeinder et al. | |
| 4,446,456 | 5/1984 | Beier | 340/802 |
| 4,488,017 | 12/1984 | Lee | 340/709 |
| 4,509,526 | 4/1985 | Barnes et al. | 128/661.1 |
| 4,523,911 | 6/1985 | Braetsch et al. | 433/101 |
| 4,571,681 | 2/1986 | Beier et al. | 364/413.28 |
| 4,586,398 | 5/1986 | Yindra | 200/86.5 |
| 4,639,710 | 1/1987 | McMillan et al. | 200/86.5 |
| 4,670,738 | 6/1987 | Weinblutt | 340/712 |
| 4,712,101 | 12/1987 | Culver | 340/710 |
| 4,830,613 | 5/1989 | Gmeinder | 433/98 |
| 4,853,687 | 8/1989 | Isomura et al. | 364/424.05 |
| 4,933,843 | 6/1990 | Scheller | 364/413.01 |
| 5,026,387 | 6/1991 | Thomas | 606/169 |
| 5,056,059 | 10/1991 | Tivig et al. | 340/712 |

FOREIGN PATENT DOCUMENTS

| | | |
|---|---|---|
| 2724051 | 12/1987 | Fed. Rep. of Germany . |
| 8109645 | 5/1981 | France . |
| 8704383 | 10/1987 | France . |
| WO89/05613 | 6/1989 | PCT Int'l Appl. . |

Primary Examiner—Alvin E. Oberley
Assistant Examiner—S. Saras
Attorney, Agent, or Firm—Hill, Steadman & Simpson

[57] ABSTRACT

A medical apparatus having a variety of electrically actuatable elements includes actuation arrangement for assisting the selection of functions of the electrically actuatable elements. The actuation arrangement includes a single actuation device, preferably a foot switch, that can be brought from an initial position into two working positions. By actuating the actuation device into one of the two working positions, function display elements provided with symbol identifiers and optical signal generators are driven in succession and are displayed on a visual field. A control arrangement processes the control signals from the signal generators, such that the optical signal generators of the function display elements are successively driven in accordance with the selected actuation direction until a desired function display element is reached. The appertaining operator elements are thereby switched in a preparatory manner. By subsequent actuation of the actuation device into the other working position, the appertaining operator element is activated.

27 Claims, 4 Drawing Sheets

MEDICAL APPARATUS, HAVING A SINGLE ACTUATING DEVICE

FIELD OF THE INVENTION

The present invention relates to medical apparatus having a single actuating device.

BACKGROUND OF THE INVENTION

In certain medical apparatus, such as x-ray, dental or ophthalmological apparatus, it is desireable to be able to expediently select various "functions", such as the positions of adjustable elements and the operating values thereof, with the assistance of electrical actuating devices. Previously, a plurality of hand and foot switches were arranged at different locations of the apparatus, and had to be individually actuated for selecting each of these "functions".

For example, in a dental apparatus it is important to select a variety of functions during the course of treating a patient, and to vary the position and operating values of elements contained in the apparatus. Such elements can include a patient chair, various instruments used by a physician or assistant, and auxiliary functions of the instruments. The functions of the elements to be selected or triggered can be divided into device functions, instrument functions, and auxiliary functions.

For example, device functions can include moving a physician's and/or assistant's instrument from a starting position into a working position and back to the starting position, bringing the entire patient chair, or parts thereof, such as a back rest, seat or head support, from a starting position into one or more working positions back to the starting position, and bringing the patient chair, or parts thereof, from a first working position into a second working position, such as an expectoration position, and from the second working position back to the first working position during treatment of a patient.

In known devices, the selection of device functions ensues by actuating appropriate switch elements, with which allocated electrical and/or hydraulic motor operators are actuated. The switch elements are usually manually actuated, and a few are actuated with a foot switch.

In addition, the instrument functions can include speed control of an instrument drive motor, such as an electric air motor or turbine, defining the rotational sense of the drive motor as clockwise or counter clockwise, defining and connecting cooling agents, such as air, water, or spray, preselecting the power of the instrument drive, and preselecting the type of control of the instrument drive, such as an on/off function or regulating function.

In known devices, the selection of the instrument functions ensue with switch or control elements arranged at a suitable location, by which the drives are directly or indirectly switched by valves, relays or the like.

Further, auxiliary functions can include actuating a drinking glass filling element of an assistant's instrument, actuating an expectorant basin, rinsing an assistant's instrument, actuating a call system, and actuating a door opener or the like.

Previously, the selection of auxiliary functions ensued by separate, manually actuatable switches, or buttons, arranged at different locations on the apparatus.

For purposes of simplification, the means for driving the different functions, such as motor operators, valves, relays, switch elements, power control parts, etc., are hereinafter generally referred to with the term "actuating".

Previously, a multitude of functions could only be selected (if they could be selected at all), by a multitude of actuation devices, arranged at different locations of a dental apparatus. With the exception of a few functions that were capable of being selected with foot switches, the selection of the most functions was usually accomplished manually.

However, the ever-increasing number of adjustable functions in medical apparatus has given rise to increasing problems in instrument manipulation, as well as in maintaining acceptable levels of hygiene, in apparatus requiring manual actuation to select various functions.

Recent attempts to solve this problem include the disclosure of a dental apparatus wherein a plurality of switch functions can be arranged on one or on a number of foot switches, having a corresponding plurality of actuation devices, such that the actuation devices are actuatable in different directions. However, overloading a foot switch with actuation elements in this way causes the foot switch to become unsurveyable and very difficult to operate.

Another attempt to solve this problem is disclosed in WO 89.05613, in which the execution both of instrument functions and auxiliary functions of a dental apparatus can be controlled and displayed at a display screen with the assistance of a microprocessor. To this end, the microprocessor is connected to a control and display unit that includes a plurality of function display fields, such that instrument and auxiliary functions can be selected and displayed. The apparatus also contains a switch that responds when a particular instrument is removed or replaced, such that switching can be undertaken from a first mode, in which the instrument is removed from its holder and only auxiliary functions associated with the particular instrument can be selected, to a second mode, upon returning all instruments to their holders or home positions, wherein instrument and/or auxiliary functions can be selected. The functions are contained in a hierarchically divided menu system that contains an overriding main menu, and one or more subsidiary instrument menus, having adjustment and regulating menus coupled thereto. The menus can be manually selected with the assistance of selection means in the form of an infrared light barrier that is allocated to every function display field.

When an instrument is removed from its holder, the deposited or removed condition of the instruments is determined with detectors, and a switch from "auxiliary function" mode to "instrument function" mode ensues. Within the selected mode, the foot switch then assumes a control function.

SUMMARY OF THE INVENTION

It is an object of the present invention to specify a medical apparatus, such as a dental apparatus, that allows the user to be able to select a plurality of different operating parameters of a number of different units of the apparatus such as set forth hereinabove in a relatively simple, sanitary and surveyable manner, without having to execute a plurality of different operating or actuating events. As used herein, "operating parameters" encompasses valves, positions and functions which can be assumed by each of the units.

One important advantage of the apparatus of the present invention is that all functions are selectable with only one actuation device, preferably a foot switch. Thus, the actuation device need only contain a single actuation element, or device, that can be brought, preferably, into two paired complementary working positions with only two degrees of freedom, by proceeding from a standby position. The two degrees of freedom can be rotary or translational degrees of freedom, such that translational movement can proceed longitudinally along the foot switch, or transversely thereto, whereas rotary movement can proceed around an upward ordinate axis, and, potentially, around a transverse axis such that an arbitrary plurality of functions can be selected with only a few adjustments. Thus, the user need use only a single operating element, or actuation device, resulting in a simple actuation of various elements of an apparatus. Such a configuration obviates the need for using a multitude of actuation devices, arranged at a plurality of different locations on the apparatus. Thus, a user of the apparatus of the present invention can merely look to the visual field of the present invention that can be arranged at a suitable location of the apparatus (for example on a physician's instrument, a cabinet, or in the region of the chair to actuate any element desired).

By combining all important functions on one visual field, and providing for operation of various functions by only a single actuation device, the medical apparatus can be easily operated. An exemplary embodiment of the present invention includes a number of important components, as set forth below.

In accordance with one illustrated embodiment of the apparatus of the present invention, the apparatus includes as a first important component, actuation means for selectively actuating electrically actuatable elements. The actuation means is preferably a foot switch. The actuation means includes a single actuation device, preferably in the form of a plate or a disc, that is preferably adjustable by movement within two degrees of freedom. Proceeding from a middle position, these movements can include tilting and swiveling motions of the actuation device. A combined swivel and rotational motion is also conceivable. Further, movement in the plane of the actuation device which can be combined with a rotatory motion is also contemplated.

A second important component of the apparatus of the present invention is the visual field. The functions that can be triggered are visually displayed on the visual field for viewing by the operator of the apparatus of the present invention. In addition, a momentary selection position can be displayed.

Although the visual field of the apparatus of the present invention can display all selectable functions, it is also conceivable to display only certain groups of selectable functions, hereinafter referred to as "information graphic blocks", on the control panel. Such a partial display is advantageous, particularly in combination with a picture screen presentation. Information graphic blocks can be visually presented in various ways. For example, in an advantageous configuration of the present invention, the visual field can be constructed using only horizontal and vertical lines, arranged symmetrically relative to a reference point or a reference line. These lines correspond to movement of the actuation device, in the vertical lines correspond to a longitudinal tilting motion, and the horizontal lines correspond to a lateral tilting motion of the actuation device. A number of modifications are conceivable with respect to the design of the visual field, some of these being set forth in greater detail below.

A third important component of the apparatus of the present invention involves control electronics. Control electronics can include a microcontroller, or microprocessor. Signals from signal generators of a foot switch are edited and displayed on the visual field, and the switch and control events with respect to the individual elements are then triggered by the edited and displayed signals. Triggering can ensue at the actuation means in various ways, either in that one of the degrees of freedom is used for triggering, or in that the actuation device has a special pressure point in one of the working positions and an "enable signal" is provided when this pressure point is exceeded.

A number of advantageous exemplary embodiments of the present invention are set forth in greater detail below with reference to the drawings.

DETAILED DESCRIPTION OF THE PREFERRED EMBODIMENTS

Figure 1:
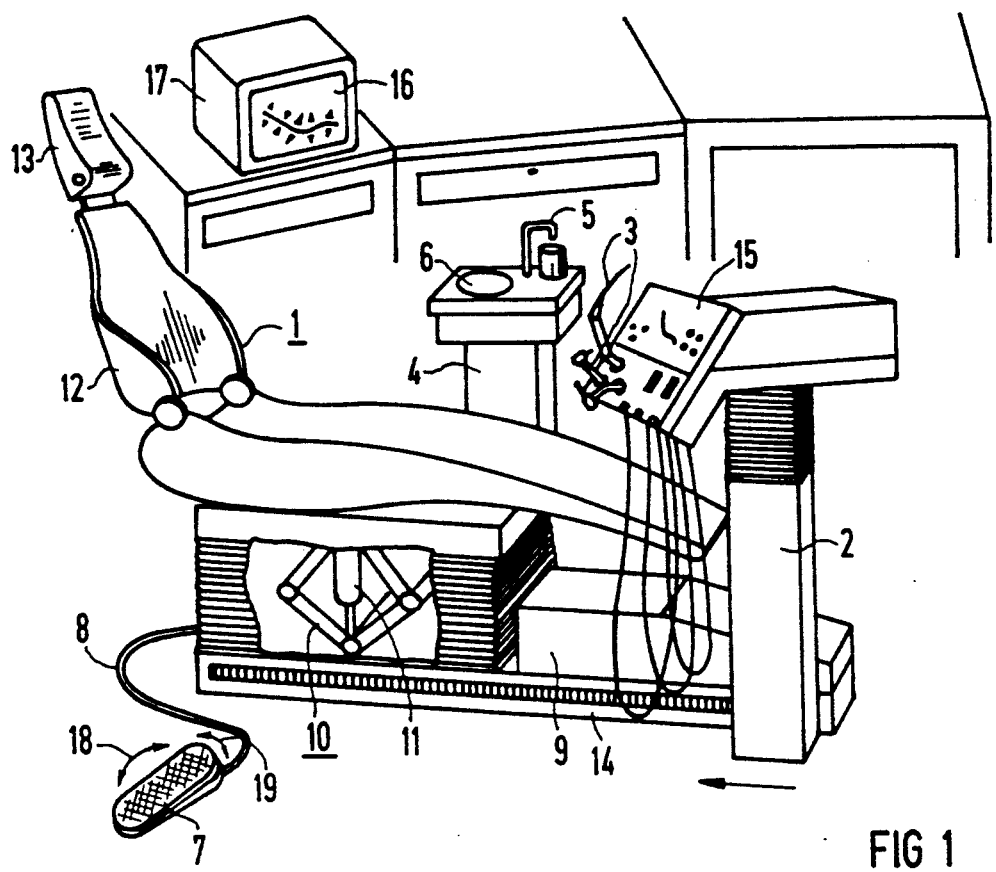
FIG. 1 is a perspective view of a dental apparatus constructed in accordance wit the principles of the present invention.

FIG. 1 illustrates a dental apparatus having a dental patient chair 1, a physician's device 2, displaceably mounted on the dental patient chair 1, where displacement of the physician's device 2 can occur in the direction of the arrow of FIG. 1. The physician's device 2 includes a plurality of instruments 3. An assistant's device 4 is stationarily or displaceably arranged at the opposite side of the dental patient chair 1 that includes a drinking glass filling element 5, and an expectorant basin rinsing element 6, where a displaceably arranged assistant's device 4 allows for displacement in the direction of the arrow of FIG. 1. The dental apparatus further includes displacement of a foot switch 7, connected by a cable 8 to a control electronics, set forth in detail hereinbelow, arranged inside the physician's device 2 or a terminal box 9.

The dental patient chair 1 can be adjusted in height with a lifting device 10, shown schematically in FIG. 1. An electric motor operator 11 is provided between articulated arms, not set forth in detail, to activate the lifting device 10. Further motor operators, not shown, for adjusting the back rest 12, the head support 13, and, if desired, further parts of the chair, are provided. The physician's device 2 is adjusted by motor-operated adjustment means (not shown). The adjustment means for adjusting the physician's device 2 is provided at the base of the chair 14, such that the physician's device 2 is capable of being moved from the illustrated disengaged position into a defined operating position in the direction of the arrow of FIG. 1 by the adjustment means.

Figure 4:
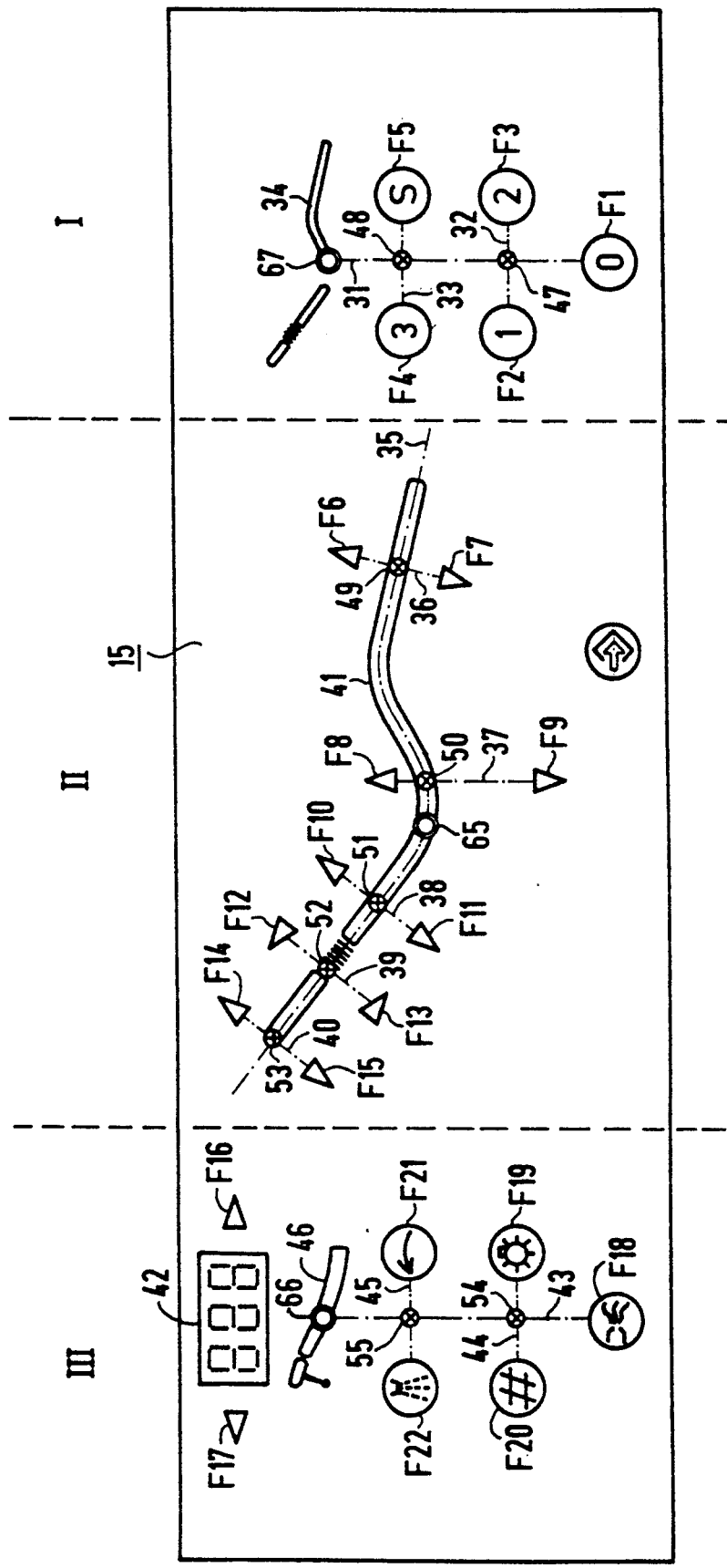
FIG. 4 is a schematic view of an informational display for use in the apparatus of FIG. 1.

A visual field 15, set forth in greater detail with reference to FIG. 4, is arranged at the front side of the operating panel of the physician's device 2.

A second visual field 16 in the form of a picture screen or monitor 17, on which certain selectable functions can be electronically displayed alternatively to, or in addition to, the visual field 15 is also provided in the field of vision of the operator. As shown in FIG. 1, the monitor 17 can be placed on a cabinet in the region of the dental patient chair 1, behind the head of the patient chair 13 or at another side of the dental patient chair 1 in the field of vision of the operator.

Figure 2:
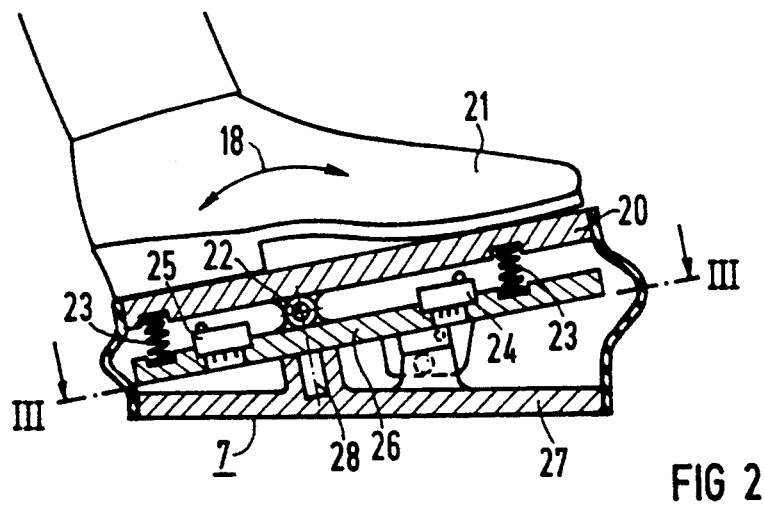
FIG. 2 is a detailed sectional view of a foot switch for use in the apparatus of FIG. 1.

As indicated by the arrows 18 and 19, a foot switch 7 can be tilted into two complementary working positions. Further details of the foot switch 7 can be seen from the sectional views of FIGS. 2 and 3. The foot switch 7 contains a plate-shaped actuation device 20, dimensioned such that the foot of an operator 21 can be fully placed thereon. A first horizontal axis 22, proceeding transversely relative to the longitudinal direction of the actuation device 20, is provided, approximately in the region of the juncture of the sole and heel of the foot of the operator 21, the actuation device 20 being capable of being moved around the horizontal axis 22 in the direction of the arrow 18 opposite spring elements 23. The foot switch 7 can thus be brought from an initial, or standby, position into two working positions, referred to below as "first complementary working position". Microswitches 24, 25 responding to a tilting motion in a forward or backward direction, are also provided in the range of adjustment of the actuation device 20.

Figure 3:
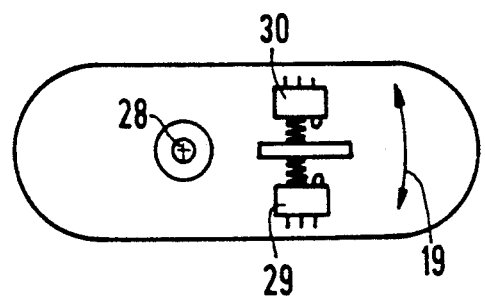
FIG. 3 is a sectional view taken generally along line III—III of FIG. 2.

An axial bearing 22 is secured to a distance plate 26 that is pivotable in the direction of the arrow 19 of FIG. 3 by a base plate 27 of the foot switch 7 around a generally vertical axial bearing 28. Two additional microswitches 29, 30 are attached in the range of pivot of the distance plate 26. All functions required for the operation of the dental apparatus can be selected or triggered with the four microswitches 24, 25 and 29, 30.

As previously mentioned, the foot switch 7 can also be made in an alternative embodiment such that a lateral tilt motion is executed, instead of the lateral swivel motion indicated by FIG. 3. It is also possible to displace the actuation device in the plate plane, i.e. forward and backward on the one hand and laterally toward the left and right on the other hand.

One of a number of possible embodiments of a visual field lying within the scope of the invention shall be set forth with reference to FIG. 4, this being arranged at the front side of the control panel of the physician's device 2 in accord with FIG. 1.

As illustrated in FIG. 4, the visual field 15 includes three information graphic blocks I, II, III, hereinafter referred to as info blocks I, II and III. The info block I serves the purpose of displaying and calling in five selectable chair programs, and correspondingly contains five function display elements F1 through F5 provided with the identifiers 0, 1, 2, 3 and S. The function display elements F1 through F5 are arranged along a reference line 31, referred to below as "limb", and along transverse lines 32, 33 departing from the reference line 31, that are referred to below as "branchings".

The function display element F1 represents the stepout of a zero position of the chair. The display elements F2 through F4 represent three freely selectable chair or working positions. The display element F5 represents a special position of the chair, for example, an expectoration position for the patient. A symbol referenced 34 of an upper part of a chair is arranged above the arrangement of the function elements F1 through F5, this being intended to make the user aware of the info block "chair positions".

The middle info block 11 serves the purpose of displaying and controlling functions allocated to the patient chair, where respective function display elements F6 through F15 are arranged along a line 35 to be referred to as "limb" and at the ends of branchings 36 through 40 departing from the limb 35. Various chair functions, such as adjusting of the upper part of the chair, adjusting the seat height, adjusting the slope of the back rest, adjusting the slope of the head support, and longitudinal displacement of the head support, can be optically displayed and called in with these function display elements. A symbolic illustration 41, in the form of an illustration of the upper part of a patient chair, emphasizes the allocation of the function display elements to the appertaining chair parts that are adjusted, and also makes it easier for the user to select the elements when an adjustment of the chair parts is to be initiated.

The left-hand info block Ill is provided for the presentation of the instrument functions. Speed of power, or intensity, values for the instrument drives, such as electric motors, air motors, turbines, electrosurgery, etc., are preselected and displayed at a display panel 42 in the upper section of info block Ill. Preselection occurs with laterally arranged function keys F16, F17 that also contain function display elements simultaneously. Functions such as "chip blower", instrument with-/without light, spray on/off, and counter clockwise/-clockwise rotational sense, are optically displayed with the function display elements F18 through F22 that are likewise arranged along a limb 43 with branchings 44, 45 branching therefrom. A symbolic illustration 46 of an instrument indicates to the user that the info block for instruments is being displayed.

In addition to containing an optical identifier, for example, in the form of an imprint or marking, the function display elements contain optical signal generators in the form of lamps, LEDS, LCDs or LCIDS, indicated at positions 47 through 55 of FIG. 4.

As shall be set forth below, further optical signal generators are expediently provided along the limbs and branchings, preferably at the intersections, in combination with the foot switch control 7, informing the user of the place at which he is now situated with respect to an input or query of information. For the sake of simplicity, these further optical signal generators are only identified in FIG. 4 with lamp symbols. In the portrayal of the info block 11, it is conceivable to provide the upper part of the chair, as schematically shown here, with light bands, section-by-section, in the region of the intersections. The intersection at which the user is situated with respect to the position of the foot switch 7 thus provides a nice optical display.

Additionally, the lines that represent the limbs and branchings need not necessarily be entered on the visual field. The lines can thus be imaginary. However, it is critical that the function display elements optically appear in a defined allocation.

Thus, it is conceivable that the neighboring function display elements illuminate or flash when an intersection is reached, until the desired function is selected via the foot switch 7.

In accordance with a further advantageous embodiment of the invention, the function display elements are combined with microswitches, this making it possible, in addition to the optical display, to also trigger a control or switching event by pressing on the surface of the function display element. It is advantageous, to this end, to configure the entire visual field as a foil keyboard, where corresponding foil switches are provided in the region of the function display elements.

The control electronics is set forth in greater detail below, including some modifications with respect to the above-explained visual field.

Figure 5:
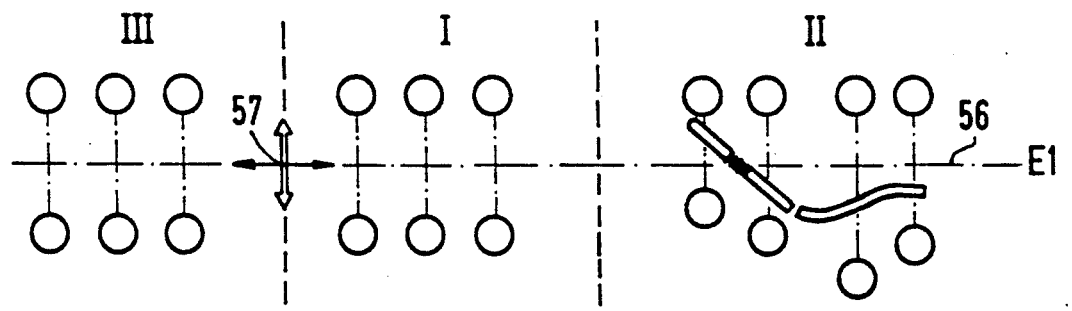
FIGS. 5 through 7 illustrate further embodiments of the informational display of FIG. 4.

As discussed above, the line presentation for the course of the limbs and branchings in an info block can proceed horizontally, vertically or obliquely. The info blocks can also be arranged next to one another in a different sequence, as illustrated in FIG. 5. For example, a common limb, such as position 56 of FIG. 5, lying in plane El, can be provided for all blocks, with the branchings, at whose ends the function display elements are situated, departing perpendicularly from this limb in an upward or downward direction. The starting point for a selection of the functions is a reference point referenced 57 that corresponds to the neutral middle position of the foot switch 7. Proceeding from this reference point, the function display elements of the info blocks can be selected along the limb 56. In the exemplary embodiment of FIG. 4, this reference point can lie at the locations of the symbolic presentations 34, 31 and 45, identified by double circles.

Figure 6:
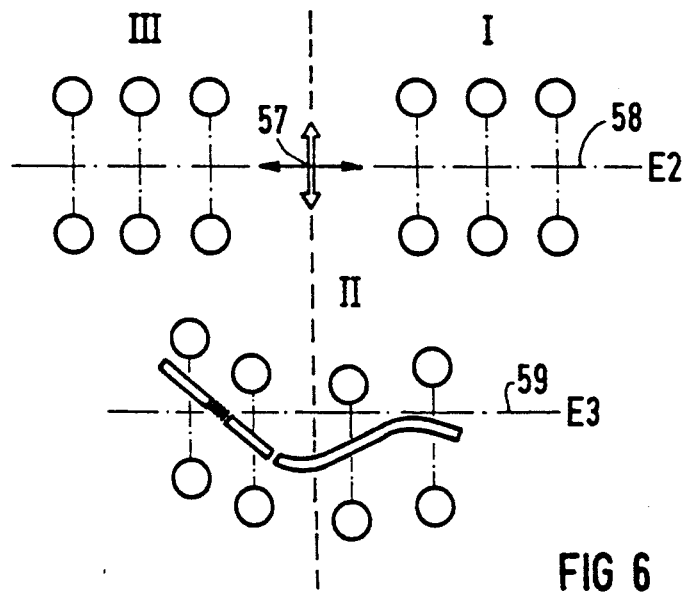

As illustrated in FIG. 6, the info blocks can also be arranged above one another in a plurality of planes. In this embodiment, the info blocks I and Ill are arranged in a common plane E2, and the info block 11 is arranged therebelow in a further plane E3. In this embodiment, the limbs 58, 59 proceed horizontally for all three info blocks. However, it is also conceivable to have the limb 59 for the info block 11 proceed in accordance with the symbolic illustration of the upper part of the chair, as illustrated in FIG. 4.

Figure 7:
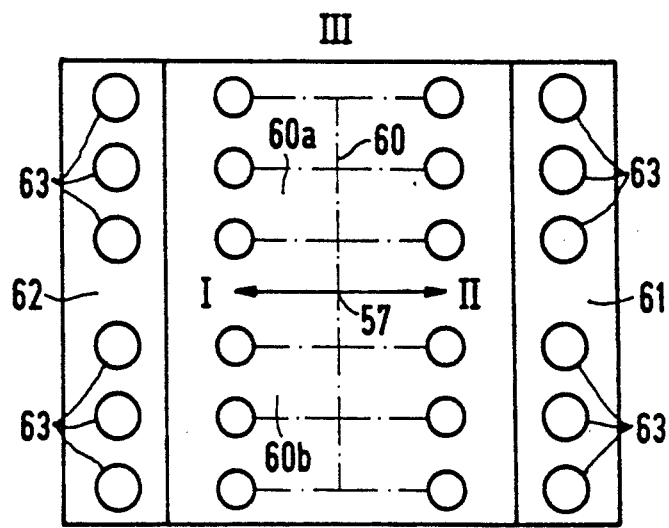

Although it is advantageous to arrange a plurality of info blocks side-by-side, such an arrangement is not required. For example, it is possible to portray only one info bock on the visual field and to subdivide this into a plurality of sub-groups. Such an arrangement is illustrated in FIG. 7, in which a vertical limb 60, proceeding from a reference point 57, contains an upper segment 60a and a lower segment 60b, each segment having various function display elements. Proceeding from the reference point 57, the info blocks I and 11 can be selected by deflecting the foot switch actuation device 20 out of the middle position. Such a display is particularly advantageous in combination with a digital image presentation via a monitor, because the visual field therein is electrically generated, and the operator can thus first have the desired info block displayed on the picture screen by calling correspondingly defined data in from a data store. Given this digital presentation, the info blocks are made visible with the assistance of appropriate software. Light spots along a limb in this embodiment can be defined by a picture screen cursor, that is moved in the direction of the function to be selected when the foot switch 7 is actuated. Compared to the embodiment set forth above, in conjunction with FIG. 6, this type of visual field presentation has the advantage that only the selected info block that the user requires is made visible. Therefore, the operator need only concentrate on a single info block. This arrangement allows for an intrinsically arbitrary number of functions to be displayed and selected in a simple manner.

As illustrated in FIG. 6, a division of the function display elements into a plurality of planes, and segments within a plane, is easily accomplished. Thus, the number of functions to be provided is theoretically unlimited. A further advantage of the apparatus of the present invention is that arbitrary functions can be readily retrofitted at a later time by appropriately modified or supplemented software. As a result of the division into various segments, meaningful functions can be combined, for example the functions for chair programs or instrument functions, where the resolution, or the demands made of the dexterity of the foot of the operator 21, is then lessened due to the correspondingly lower number of planes per segment.

When displaying the visual field by a picture screen, it is especially advantageous to arrange a foil keyboard or a "touch screen" on the picture screen. The addition of such a touch screen makes it possible to also control the individual functions of the apparatus by hand. The visual field can also be provided with "soft keys" that, for example, are laterally arranged, as illustrated in FIG. 7. The "soft keys" can serve the purpose of manual actuation of the functions displayed on the picture screen at, for example, positions 61 through 63. The actuation here can ensue via foil keys 63.

Further, the individual info blocks can be electrically coupled in to the removal of the instruments from their respective storage receptacles, such that, for example, only info block I or 11 appears on the picture screen when the instruments are put down, and only the instrument-related info block Ill appears when an instrument is in use. The light spot or, starting point, for selecting the individual function display elements would then automatically skip to the starting or reference point of the selected and displayed info block such as, for example, info block 111. When the instrument is placed back down, the light spot automatically skips back to the starting or reference point of info block I or 11.

The control electronics of the apparatus of the present invention, are set forth below in conjunction with the drawings of FIGS. 8, 9, and 10.

Figure 8:
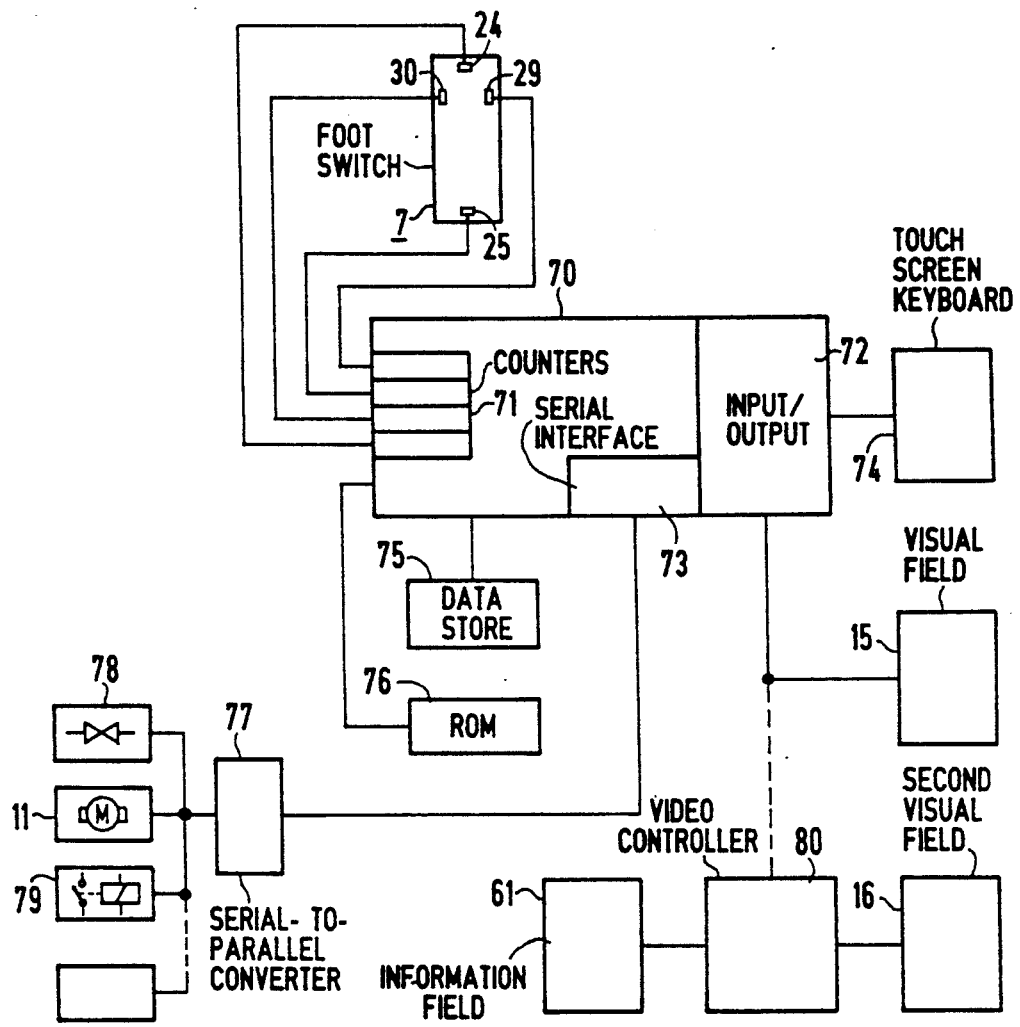
FIG. 8 illustrates a block circuit diagram for the control electronics for the apparatus of FIG. 1.
Figures 9, 10:
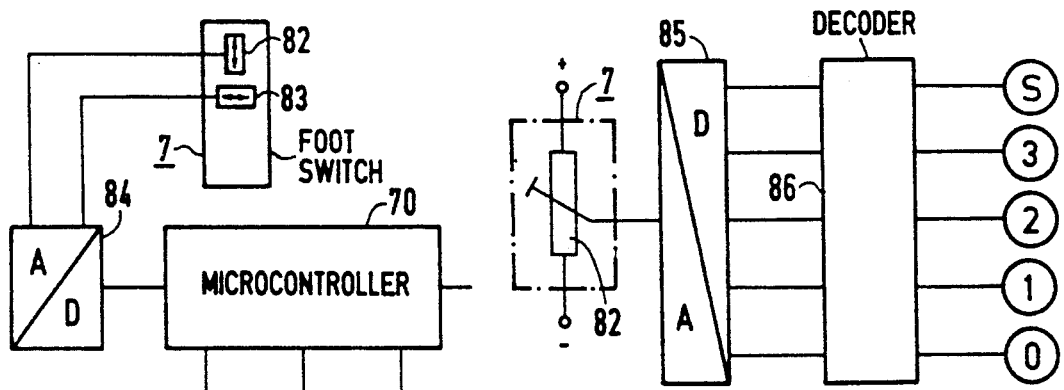
FIG. 9 illustrates another exemplary embodiment of a block circuit diagram for the control electronics.
FIG. 10 illustrates a diagram of a circuit for achieving an electronic skip function in the control electronics.

As illustrated in FIG. 9, the "heart" of the control electronics is a microcontroller 70, having a plurality of counters 71, an input/output part 72, and a serial interface 73, where the counters 71, input/output part 72, and serial interface 73 are illustrated in FIG. 8. A foil keyboard or "touch screen" keyboard 74, illustrated in FIG. 8, includes corresponding switches, with which desired functions to be manually selected can be triggered at the locations of the function display elements on the visual field 15 of FIG. 8, and is connected to the input/output part 72 of the microcontroller 70. The visual field is in the form of, for example, an LED display, and is connected to the output part 72 of the microcontroller 70.

Four counters 71 are provided in the exemplary embodiment for the signal generators, or microswitches 24, 25, 29, and 30. It is also conceivable to combine two counters into one, where every counter operates bidirectionally.

A data store 75 and a read-only memory 76, both illustrated in FIG. 8, are connected to the microcontroller 70. The individual operator elements are connected to the serial interface 73 via a serial-to-parallel converter 72, which can have corresponding power stages. These operator elements can include, for example, a valve 78 for controlling the flow of, for example, drive air for a drive motor of a dental handpiece, a motor operator 1 1 as set forth above in reference to FIG. 1, with which the lifting means 10 for adjusting the height of the dental patient chair 1 can be actuated , or a relay 79 for activating an electric drive motor.

Further, when using a picture screen as a visual field, it is advantageous to connect a video controller 80 and an image storage device 81 to the output part 72 of the microcontroller 70.

As illustrated in FIG. 9, rather than use the four microswitches 24, 25, 29 and 30, optical, magnetic or electrical, path-dependent position encoders can be provided in the foot switch 7, these encoders delivering a position-dependent quantity to a displacement of the actuation device 20 from the standby position. In this illustration, only two position encoders 82, 83 are required. Where analog position encoders, are used that can be displaced out of a middle position, such as potentiometers, an analog-to-digital converter 84 would also have to be added to convert the analog signals into digital signals. Further processing of the data, or the read-in, ensues analogous to the block circuit diagram of FIG. 8. It is also contemplated with respect to FIG. 8 that the activation can ensue with an additional microswitch, or by a pedal pressure switch.

The advantage of the circuit diagram illustrated in FIG. 9 is that the motion of a light spot along a limb does not proceed step-by-step with a prescribed speed, but is defined by the speed of actuation of the actuation device 20 at the foot switch 7. Thus, faster operation and control are made possible. Moreover, functions can be set to be infinitely variable, and proportional to the motion of the foot switch 7. Thus, the speed of a motor operator, the power of a device for removing dental calculus, or the power of a high-frequency surgical device can be quickly brought to a desired speed or power, or operated at a variable speed or power, if so desired.

Further, the use of desired information elements can insure operation with continuous variation or, in accordance with an electrical skip function, can proceed step by-step along a limb or from plane to plane. Such a step-by-step display is illustrated in the schematic circuit diagram of FIG. 10, in which an analog foot switch signal is supplied by a position encoder, such as the position encoder 82 in FIG. 9, to an analog-to-digital converter 85. The analog-to-digital converter 85 is connected to a decoder 86. The outputs of the decoder 86 are connected to the function display elements, such as, for example, function display elements F1 through F5 of FIG. 4. The functioning of the control means is set forth in greater detail below with reference to the visual field presentation of FIG. 4.

After the power supply is switched on, the microcontroller 70 produces a standby condition. The data provided for producing the standby condition is taken from the data store 75. The counters 71 are either at an average value or at zero. When the actuation device 20 of the foot switch 7 is then moved from the basic or standby position into the first complementary working position, one of the microswitches 24, 25, 29, or 30 is activated, and the counter or counters 71 begin to run in the direction corresponding the actuation direction. The frequency with which the counter runs can be prescribed or set by the customer.

The output 72 of the microcontroller 70 then moves a light spot from a defined starting point on the visual field 15, or simulates the motion of the light spot by driving corresponding LEDS. The starting point can be freely selected. For example, in the exemplary embodiment of FIG. 4, the starting point, can be provided at the location referenced as position 65. When departing the info block 11, the light spot automatically skips to one of the reference points 66, 67 of the neighboring info blocks I or 11.

When a picture screen display is used, the image formatting and the offering of the video signals are generated by the video controller 80. After being switched on, the microcontroller 70 forwards the image data from the data store 75 to the video controller 80, that deposits the data in the storage device 81. The movement of the light spot along an information limb is realized by modifying the data during operation.

With the assistance of the foot switch 7, the operator first moves the light spot from the defined starting position along a limb until reaching the intersection at which the desired function display element is situated. The control signals from the signal generators are then processed in the control electronics, such that the optical signal generators are successively driven, and the appertaining operator elements are switched into a prepared mode. Upon movement of the foot switch 7 into the second working position, an activation signal is forwarded to the appertaining operator element, and the desired function is then triggered and displayed. The selected location can also be acknowledged for the operator by an optical signal, such as a flashing light, or by an acoustic signal, such as a voice output. The activation of a selected function can proceed following a defined delay time for safety after the actuation device 20 is released. The triggering of an activation signal can also proceed by an additional microswitch that, preferably, responds in a middle position of the actuation device 20 given actuation. After the actuation device 20 is released, it returns to its standby position, where the display skips back to the starting or reference point.

When a selected function is activated, the microcontroller 70 writes the operating values into the nonvolatile read-only memory 76. It is thereby assured that the operating condition is preserved given a potential possible line outage. In the event that a power outage occurs, the operator can continue to work with the function chosen before the outage. The power parts and, thus, the operator elements, are simultaneously informed of which function or functions are to be executed, and how they are to be executed by the serial interface 73.

Given use of a foil keyboard, this is constantly integrated by the input part 72, so that the appertaining operator element is automatically driven by the serial interface 73, given actuation of one of the function display elements.

It is not required that the light spot be conducted along a limb between the function display elements, arranged in complimentary fashion, as it is also contemplated that the light spot be co-integrated into the function display elements. Thus, for example, two respective function display elements allocated to one another in complimentary fashion, can simultaneously light or flash and are then relayed step-by-step in pairs until the desired, selected function display element is reached by actuating the foot switch 7 in the other working direction. When this condition is reached, only one function display element is still lit.

Although other modifications and changes may be suggested by those skilled in the art, it is the intention of the inventor to embody within the patent warranted hereon all changes and modifications as reasonably and properly come within the scope of his contribution to the art.

I claim:

1. A medical apparatus comprising:
   a plurality of different physically elements, including device, instrument, and auxiliary functions, each having respective, variable operating and positioning parameters associated therewith;
   a single, user-manipulatable actuation element moveable in a manipulation range from a standby position successively to at least first and second working positions for selecting said operating parameters;
   user-operable control signal generator means connected to said actuation element and to said actuatable elements for supplying respective control signals to said actuatable elements to set said variable operating parameters;
   visual display means for displaying a plurality of display elements corresponding to said actuatable elements and said operating parameters, and representing one of said device, instrument, and auxiliary functions to be selected;
   optical signal generator means connected to said control signal generator means and connected to said display means causing successive display of each display element corresponding to an actuatable element and the selected operating parameters for that actuatable element, said display elements being arranged on said visual display means along at least one limb on said visual display means and forming at least one information graphic block with said optical generator means on said visual display means; and
   electronic control means connected to said actuation element, said actuatable elements, said control signal generator means, said optical signal generator means, and to said display means for driving said optical signal generator means to display said display elements in a succession when said actuatable element is in said first position to assist an operator in selecting said operating parameters via said control signal generator means, and for thereafter enabling operation of a selected, displayed actuatable element, at the selected operating parameters, only when said actuation element is moved to said second position.

2. The apparatus of claim 1, said actuation element further comprising a foot switch having a bidirectional plate-shaped actuation device of sufficient size to permit said operator to fully place a foot of said operator on said bidirectional plate-shaped actuation device.

3. The apparatus of claim 2, said bidirectional plate-shaped actuation device having first and second directions for movement in a plane, wherein said first direction is substantially perpendicular to said second direction.

4. The apparatus of claim 3, wherein said actuation element is pivotally seated about an axis, said axis being substantially vertical to said plane.

5. The apparatus of claim 1, said actuation element further comprising a horizontal axis and a vertical axis, said actuation element being arranged movably around said horizontal axis, proceeding transversely relative to a longitudinal axis of said actuation element, and said vertical axis arranged perpendicularly to said longitudinal axis.

6. The apparatus of claim 5, wherein said horizontal axis and said vertical axis are arranged over ⅓ of said length of the plate-shaped actuation device of said actuation element.

7. The apparatus of claim 1, wherein said actuation element is coupled to path-dependent encoders that, dependent on a displacement of the actuation element, effect a drive of said optical signal generator means.

8. The apparatus of claim 1, further comprising an additional switch element coupled to said actuation element, said actuation element further comprising an increased pressure point, said additional switch element being triggered when movement of said actuation element exceeds said increased pressure point.

9. The apparatus of claim 1, wherein said display elements arranged on said visual display means along said at least one limb are arranged on a limb that is imaginary on said visual display means.

10. The apparatus of claim 1, wherein said display elements arranged on said visual display means along said at least one limb are arranged on a limb that is optically perceptible on said visual display means.

11. The apparatus of claim 9, wherein said display elements are arranged at branchings that depart from said limb.

12. The apparatus of claim 10, wherein said display elements are arranged at branchings that depart from said limb.

13. The apparatus of claim 9, further comprising a reference point allocated to an initial position of said actuation element, said optical signal generator means being driven proceeding form said reference point.

14. The apparatus of claim 10, further comprising a reference point allocated to an initial position of said actuation element, said optical signal generator being driven proceeding from said reference point.

15. The apparatus of claim 1, said visual display means further comprising a monitor and at least one information graphic block, said information graphic block including at least one of said display elements of said visual display means and being portrayable on a picture screen of said monitor.

16. The apparatus of claim 15, said picture screen of said monitor further comprising a touch screen keyboard, having an arrangement of switch surfaces that corresponds to an arrangement of said function display elements of said information graphic block to be portrayed.

17. The apparatus of claim 1, further comprising a graphic symbol representation of at least one actuatable element allocated to said display elements, and an information graphic block including at least one of said display elements of said visual display means.

18. The apparatus of claim 17, wherein said graphic symbol representation is arranged along a reference line of said information graphic block, said information graphic block further comprising upper and lower graphic block segments, said upper and lower graphic block segments being divided by said reference line.

19. The apparatus of claim 1 further comprising a plurality of information graphic blocks arranged sideby-side on said visual display means, said information graphic blocks including at least one of said display elements of said visual display means.

20. The apparatus of claim 19, said information graphic blocks further comprising a common reference line forming a limb on said visual display means.

21. The apparatus according to claim 19, said visual display means further comprising a plurality of planes, said plurality of information graphic blocks being divided onto said plurality of planes, and said plurality of planes having a plurality of limbs.

22. The apparatus of claim 1, further comprising a reference point, at least one information graphic block including at least one of said display elements, and having a vertical line that forms a limb, horizontal lines having ends at which said optical signal generator means of said display elements are arranged branching off from said vertical line at defined intervals proceeding from said reference point.

23. The apparatus of claim 22, further comprising additional optical signal generator arranged at intersections of said limb and said horizontal lines.

24. The apparatus of claim 1, said electronic control means further comprising a microcontroller.

25. The apparatus of claim 24, said microcontroller further comprising at least one pulse counter, said pulse counter being allocated to said signal generator means, said pulse counter being capable of being driven with a predetermined frequency, said pulse counters successively driving said optical signal generator means on a limb of an information graphic block, said information graphic block including at least one display element, upon receipt of a signal corresponding to an actuation of said actuation element in the direction of said second working position.

26. The apparatus of claim 24, further comprising a video controller connected to an output of said microcontroller for formatting an image of an information graphic block of said visual display means and video signals at said picture screen, wherein image data are forwarded from an image storage device through said video controller to an image storage device upon activation of initial said medical apparatus.

27. The apparatus of claim 2, wherein said foot switch is adjustable into four working positions, proceeding from a middle position, that are complimentary in pairs.

* * * * *